(12) United States Patent
Ferguson et al.

(10) Patent No.: US 11,160,632 B1
(45) Date of Patent: Nov. 2, 2021

(54) HIGHLY EFFICIENT MEDICAL HEADLAMP

(71) Applicant: RIVERPOINT MEDICAL, LLC, Portland, OR (US)

(72) Inventors: John Thomas Ferguson, Portland, OR (US); Ned Nestorovic, Woodinville, WA (US); Jack Schmidt, Woodinville, WA (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 25 days.

(21) Appl. No.: 16/742,669

(22) Filed: Jan. 14, 2020

(51) Int. Cl.
*A61B 90/35* (2016.01)
*F21V 21/084* (2006.01)
*F21W 131/205* (2006.01)
*A61B 90/30* (2016.01)

(52) U.S. Cl.
CPC ............ *A61B 90/35* (2016.02); *F21V 21/084* (2013.01); *A61B 2090/309* (2016.02); *F21W 2131/205* (2013.01)

(58) Field of Classification Search
CPC ......... A61B 1/06; A61B 1/0607; A61B 1/063; A61B 1/0646; A61B 2090/309; A61B 90/35; F21V 21/084; F21W 2131/20; F21W 2131/205
See application file for complete search history.

(56) References Cited

U.S. PATENT DOCUMENTS

| | | | | |
|---|---|---|---|---|
| 5,774,271 | A * | 6/1998 | Lagerway | F21L 14/00 359/649 |
| 6,955,444 | B2 | 10/2005 | Gupta | |
| 8,047,684 | B2 * | 11/2011 | Chang | F21V 14/065 362/268 |
| 10,107,483 | B2 * | 10/2018 | Oren | F21V 15/01 |
| 10,174,912 | B1 * | 1/2019 | Ferguson | F21V 11/10 |
| 10,708,990 | B1 * | 7/2020 | Ferguson | A61B 90/30 |
| 2012/0120635 | A1 * | 5/2012 | Strong | F21V 5/008 362/105 |
| 2014/0334157 | A1 * | 11/2014 | Ferguson | F21V 11/10 362/277 |

* cited by examiner

*Primary Examiner* — Leah Simone Macchiarolo
(74) *Attorney, Agent, or Firm* — Timothy E. Siegel Patent Law, PLLC; Timothy E. Siegel

(57) ABSTRACT

A high-efficiency medical headlamp, emitting light from a front surface, and having a high-efficiency light source, producing a first light beam. An iris assembly has an annular body that defines a first annulus and has iris blades which can be extended into the annulus to form a second, smaller, annulus. This iris assembly is positioned relative to the light source so that the iris blades are in front of the high-efficiency light source. The annular body and therefore the first annulus have finite depth from back to front. A light guide is placed immediately behind the iris blades and defines a channel that is open at its back and its front and has a reflective interior surface, with the open back being transversely coincident to the light source so that light from the light source can travel through the channel to and out from the open front.

15 Claims, 4 Drawing Sheets

HIGHLY EFFICIENT MEDICAL HEADLAMP

BACKGROUND OF THE INVENTION

In the design of medical headlamps, it is critically important to avoid wasting light. The more of the light that is produced by the light source, that actually is emitted from the front of the lamp, the longer the battery life per unit of battery charge. Accordingly, a highly efficient headlamp may permit the use of smaller, lighter batteries or permit more time to pass, before the batteries must be changed. Both improvements are highly desirable as reducing battery weight may add to the comfort of the surgeon and increasing time between battery changes reduces an extra set of actions during surgery, which can only serve to complicate an already complicated surgical theater.

Creating a highly efficient headlamp that also permits an adjustment of beam width is a particular challenge, as the iris that is necessary in this type of headlamp, naturally complicates the design and tends to result in some light being blocked or otherwise not being emitted from the front end of the headlamp. It is very difficult to position the light source close to the iris blades, and even if done the light beam will not have spread out as far as is desirable by the time it reaches the iris. But if the light source is positioned behind the iris blades by more than a centimeter, some of the light will be lost.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a high-efficiency medical headlamp, emitting light from a front surface, and having a high efficiency light source, producing a first light beam. Further, an iris assembly has an annular body that defines a first annulus and has iris blades which can be extended into the annulus to form a second annulus, smaller than the first annulus. This iris assembly is positioned relative to the light source so that the iris blades are in front of the high efficiency light source. The annular body and therefore the first annulus have finite depth from back to front. A light guide is placed immediately behind the iris blades and defines a channel that is open at its back and its front and has a reflective interior surface, with the open back being transversely coincident to the light source so that light from the light source can travel through the channel to and out from the open front.

In a second separate aspect, the present invention may take the form of a high-efficiency medical headlamp, emitting light from a front surface, and having an aft barrel defining a radial slot. This aft barrel holds a high-efficiency light source; an iris mechanism, having an annular body defining an annulus and iris blades extending into the annulus, the iris blades placed in front of the high-efficiency light source, and a stem extending outwardly from the annular body through the radial slot, and wherein moving the stem moves the iris blades in or out in the annulus. A lens train package is partially set into the aft barrel and has a round tube, expanding transversely outwardly from back to front, and defining lens positions, with an optical train of lenses set into the round tube.

In a third separate aspect, the present invention may take the form of medical headlamp, including a housing, having a front and a back, defining a front lens seat, near the front and having threading in front of the front lens seat. There is a light source in the housing and a front lens, from which light is emitted, is seated in the front lens seat. Further, a threaded front lens holder screwed into the threading of the housing, and abuts the front lens, thereby pressing the front lens against the front lens seat.

BRIEF DESCRIPTION OF DRAWINGS

Various embodiments of the invention are disclosed in the following detailed description and accompanying drawings.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms ["back" and "front" ] are used to describe the disclosed embodiments. The terms are used consistently with the description of the exemplary applications and are in reference to the front surface being the surface from which light is emitted.

Figure 1:
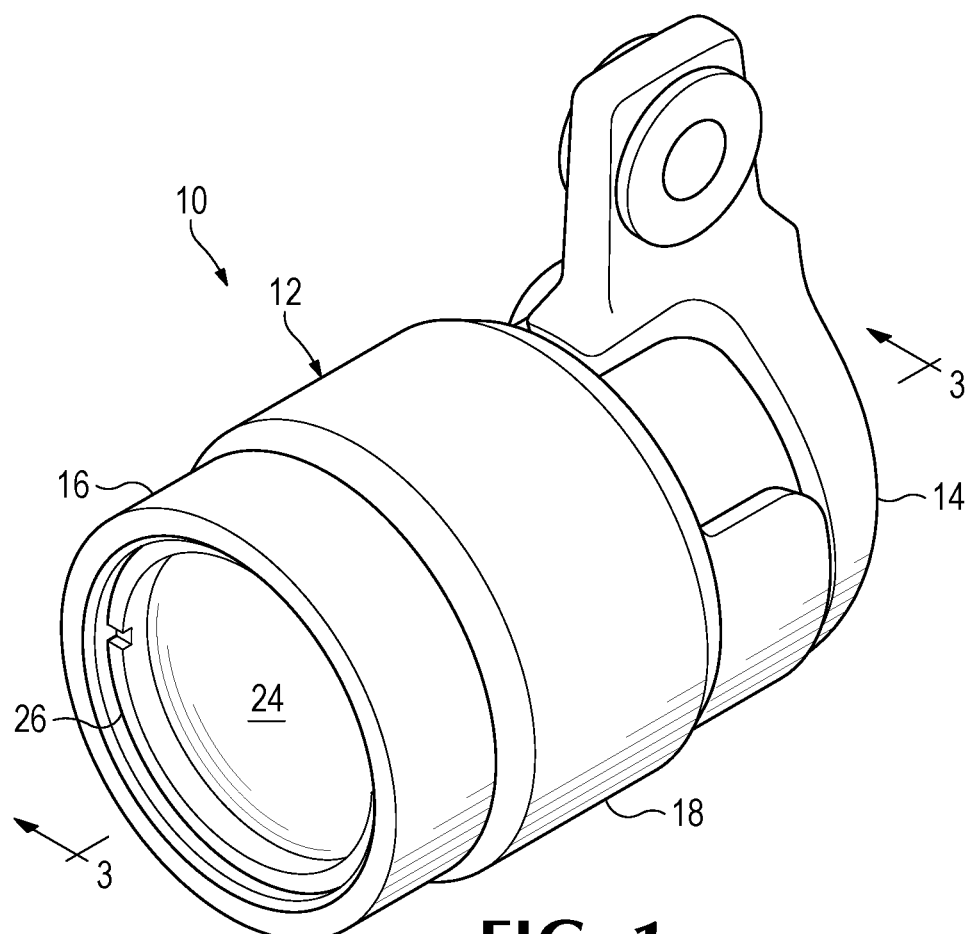
FIG. 1 is an isometric front side view of a medical headlamp, according to the present invention.

Referring to FIG. 1, a medical headlamp 10 includes a housing 12, made up of an aft barrel 14, a lens train holder 16 and an iris actuation ring 18. Lens train holder 16 defines circumferential seats for a prime lens 20, an intermediate lens 22 (on FIGS. 2 & 3), in the form of an achromatic doublet, and a front lens 24. A set of threaded lens holders 26 screw into threads defined by holder 16 for each lens, thereby for each lens 20, 22 and 24 pressing said lens against its lens seat. For the front lens this arrangement seals said housing against the intrusion of liquid, for example blood that may shoot out from a patient during an operation, or a cleaning solution used to clean headlamp 10.

Figure 2:
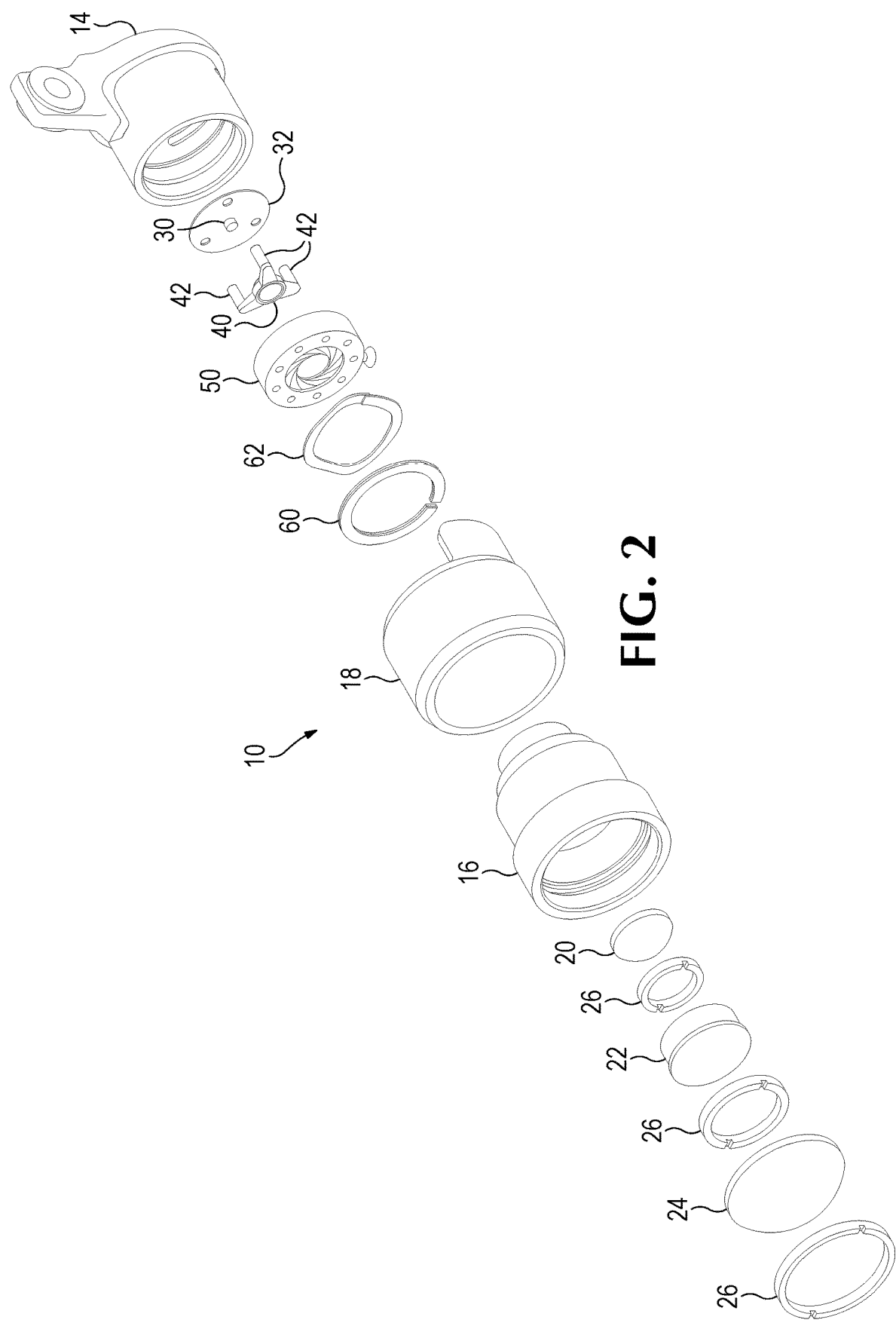
FIG. 2 is an exploded view of the medical headlamp of FIG. 1
Figure 3:
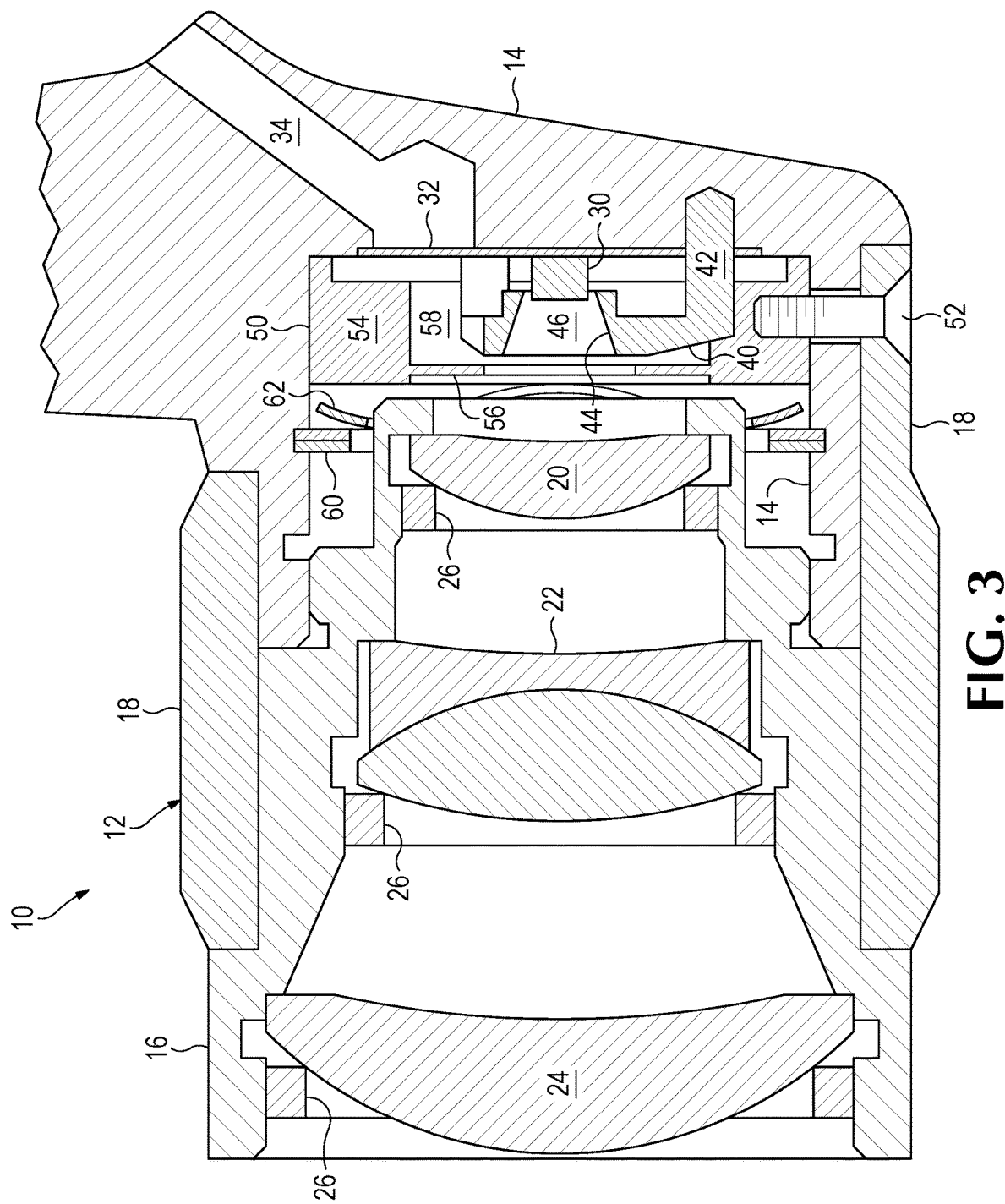
FIG. 3 is a sectional view of the medical headlamp of FIG. 1, taken along line 3-3 of FIG. 1.

Actuation ring 18 can be rotated to change the size of the beam of light emitted and therefore of the spot of light created by the beam. Referring, now, to FIGS. 2 and 3, light is created by a high-efficiency light source in the form of a light emitting diode (LED) 30. A substrate 32 supports LED 30 and supplies it with electricity by way of conductive traces (not shown) and also provides a pathway for heat to travel from LED 30 to housing 12, where it can travel through the metallic housing and radiate out from the housing surfaces. Electricity is delivered to substrate 32 by wires (not shown) extending through a passageway 34 in housing 12.

A light guide member 40 has three legs 42 that engage with matching holes defined in the aft-barrel 14, extending through apertures in substrate 32. This structure supports a light guide 44, which defines a channel 46, open at its front and back, and having a reflective interior surface. The front of LED 30 extends into the rear portion of channel 46. Further an iris 50, permits a user to change the width of the light beam that is emitted from the front lens 24. An iris actuation pin 52 is engaged to ring 18, permitting a user to adjust the iris by rotating ring 18. Iris blades 56 move inwardly or outwardly from annular housing 54, according to the position of pin 52, creating a smaller or larger light spot. Annular housing 54 defines an annulus 58, with blades 56 creating a smaller annulus. Annulus 58 has depth, and light guide 44 fits entirely in it. Placing light guide 44 and therefore channel 46 into annulus 58 brings it close to iris blades 56 prevents a loss of light and creates a more powerful beam than would otherwise be the case. A pair of washers 60, bracing a wave spring 62, maintain pressure on iris annular housing 54, maintaining its position and preventing it from rotating.

Figure 4A:
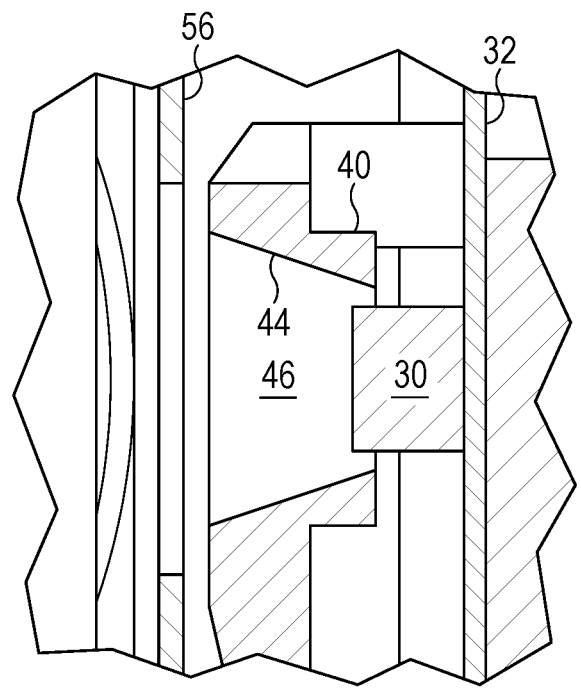
FIG. 4A is a sectional detail view of the light source and light guide of FIG. 3.
Figure 4B:
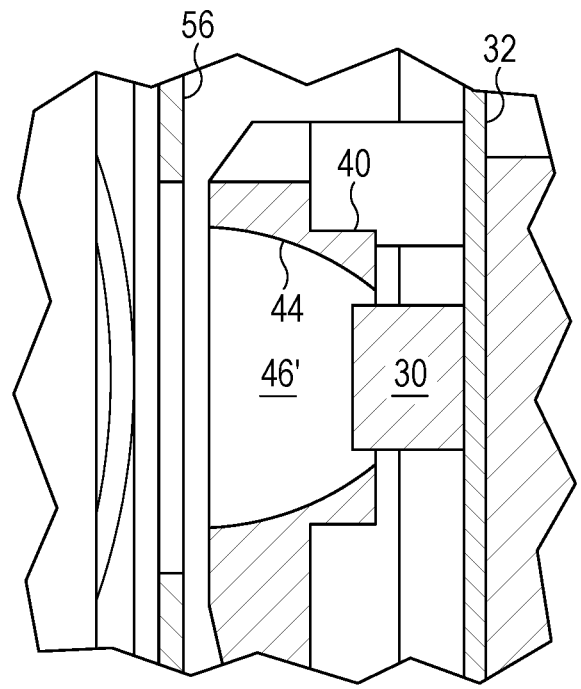
FIG. 4B is a sectional detail of a light source and light guide of an alternative embodiment of a medical headlamp that is otherwise the same as that of FIG. 3.

Referring to FIG. 4A, in a preferred embodiment channel 46 is in the form of a truncated cone. In an alternative preferred embodiment, shown in FIG. 4B, channel 46' is in the form of a parabola section. Other shapes are possible, including a circular cylinder. In a preferred embodiment channel 46 is transversely circular, but in alternative embodiments channel 46 is transversely a polygon.

The use of achromatic doublet lens 22 prevents chromatic aberrations, which may occur with other lens configurations. In some embodiments, a color variable LED is used for LED 30.

The disclosed embodiments are illustrative, not restrictive. While specific configurations of medical headlamps have been described, it is understood that the present invention can be applied to a wide variety of optical technology. There are many alternative ways of implementing the invention.

What is claimed is:

1. A high-efficiency medical headlamp, emitting light from a front surface, and comprising:
   a) a high efficiency light source, producing a first light beam;
   b) an iris assembly, having an annular body defining a first annulus and iris blades which can be extended into said annulus to form a second annulus, smaller than said first annulus, said iris assembly positioned relative to said light source so that said iris blades are in front of said high efficiency light source, said annular body and therefore said first annulus having finite depth from back to front; and
   c) a light guide placed immediately behind said iris blades and defining a channel that is open at its back and its front and having a reflective interior surface, said open back being transversely coincident to said light source so that light from said light source can travel through said channel to and out from said open front, and wherein said light guide is at least in part inside said first annulus.

2. The high-efficiency medical headlamp of claim 1, wherein said channel expands outwardly as it extends from back to front.

3. The high-efficiency medical headlamp of claim 2, wherein said reflective interior surface is in the shape of a truncated cone.

4. The high-efficiency medical headlamp of claim 2, wherein said reflective interior surface is in the shape of a parabola.

5. The high-efficiency medical headlamp of claim 1, wherein said high-efficiency light source is an LED assembly.

6. The high-efficiency medical headlamp of claim 1, wherein said high-efficiency light source has a front portion that is inside said channel.

7. The high-efficiency medical headlamp of claim 1, wherein said channel defined by said light guide is entirely inside said first annulus.

8. The high-efficiency medical headlamp of claim 1, wherein said channel is transversely round.

9. A high-efficiency medical headlamp, emitting light from a front surface, comprising:
   a) an aft barrel defining a radial slot and, holding:
      i. a high-efficiency light source;
      ii. an iris mechanism, having an annular body defining an annulus and iris blades extending into said annulus, said iris blades placed in front of said high-efficiency light source, and a stem extending outwardly from said annular body through said radial slot, and wherein moving said stem moves said iris blades in or out in said annulus, and
   b) a lens train package partially set into said aft barrel, in front of said iris mechanism, and having:
      i. a round tube, expanding transversely outwardly from back to front, and defining lens positions; and
      ii. an optical train of lenses set into said round tube.

10. The high-efficiency medical headlamp of claim 9, further having an adjustment rotatable slider, attached to said stem, and rotatable about said aft barrel.

11. The high-efficiency medical headlamp of claim 9, wherein said rotatable slider is blocked from rotating as far as the range of rotation of said stem, so that said rotatable slider does not stress said iris by pushing said stem at the end of said stem's range of rotational motion.

12. The high-efficiency medical headlamp of claim 9, wherein said round tube defines a lens seat for each lens in said optical train.

13. The high-efficiency medical headlamp of claim 9, said round tube defines a threading for a forwardmost one of said optical train of lenses and wherein a threaded lens holder is screwed into said threading, thereby retaining said forwardmost one of said optical train of lenses against said lens seat.

14. The high-efficiency medical headlamp of claim 9, wherein said set of lenses includes three lenses forming an optical train.

15. The high efficiency medical headlamp of claim 14, wherein the middle lens of said three lenses is a doublet achromatic lens.

* * * * *